United States Patent
Fujiwara et al.

(10) Patent No.: US 8,679,240 B2
(45) Date of Patent: *Mar. 25, 2014

(54) ALLERGEN INHIBITOR, ALLERGEN-INHIBITING PRODUCT, ALLERGEN INHIBITING METHOD, AND USE AS ALLERGEN INHIBITOR

(71) Applicant: Sekisui Chemical Co., Ltd., Osaka (JP)

(72) Inventors: Akihiko Fujiwara, Shimamoto-cho (JP); Taro Suzuki, Shimamoto-cho (JP); Mitsuhito Teramoto, Shimamoto-cho (JP)

(73) Assignee: Sekisui Chemical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/870,055

(22) Filed: Apr. 25, 2013

(65) Prior Publication Data

US 2013/0236528 A1   Sep. 12, 2013

Related U.S. Application Data

(62) Division of application No. 12/808,450, filed as application No. PCT/JP2008/073007 on Dec. 17, 2008, now Pat. No. 8,454,735.

(30) Foreign Application Priority Data

Dec. 17, 2007 (JP) .................. 2007-325293
Jul. 24, 2008 (JP) .................. 2008-191502

(51) Int. Cl.
*A61L 9/00* (2006.01)
*B01D 46/00* (2006.01)

(52) U.S. Cl.
USPC ........... 96/226; 55/524; 55/527; 422/1; 422/4

(58) Field of Classification Search
USPC ........................ 55/524, 527; 96/226; 442/59; 525/333.5; 526/240; 422/1, 4
See application file for complete search history.

(56) References Cited

U.S. PATENT DOCUMENTS

| | | | |
|---|---|---|---|
| 4,359,555 A | 11/1982 | d'Hondt et al. | |
| 4,448,935 A | 5/1984 | Iovine et al. | |
| 5,243,006 A | 9/1993 | Nakabayashi et al. | |
| 7,044,993 B1 | 5/2006 | Bolduc | |
| 7,431,945 B2 | 10/2008 | Ban et al. | |
| 7,520,923 B2 | 4/2009 | Marcoon | |
| 8,454,735 B2 * | 6/2013 | Fujiwara et al. | 96/226 |
| 2003/0205137 A1 | 11/2003 | Bolduc | |
| 2005/0095222 A1 | 5/2005 | Suzuki et al. | |
| 2006/0117729 A1 | 6/2006 | Bolduc | |
| 2007/0093593 A1 | 4/2007 | Krauter et al. | |
| 2007/0131116 A1 | 6/2007 | Inagaki et al. | |
| 2007/0160567 A1 | 7/2007 | Suzuki et al. | |
| 2007/0175195 A1 | 8/2007 | Skirius et al. | |
| 2008/0022645 A1 | 1/2008 | Skirius et al. | |
| 2008/0083337 A1 | 4/2008 | Yamanaka et al. | |
| 2008/0096450 A1 | 4/2008 | Goldberg | |
| 2008/0110342 A1 | 5/2008 | Ensor et al. | |
| 2008/0302243 A1 | 12/2008 | Byrd et al. | |
| 2009/0280337 A1 | 11/2009 | Semetey et al. | |

FOREIGN PATENT DOCUMENTS

| | | |
|---|---|---|
| EP | 1 703 014 | 9/2006 |
| JP | 61-44821 | 3/1986 |
| JP | 4-090762 | 3/1992 |
| JP | 04-090762 | 3/1992 |
| JP | 6-279273 | 10/1994 |
| JP | 7-171387 | 7/1995 |
| JP | 11-035629 | 2/1999 |
| JP | 11-292714 | 10/1999 |
| JP | 2001-354573 | 12/2001 |
| JP | 2003-079756 | 3/2003 |
| JP | 2003-081727 | 3/2003 |
| JP | 2003-081842 | 3/2003 |
| JP | 2003-096670 | 4/2003 |
| JP | 2003-313778 | 11/2003 |
| JP | 2004-107493 | 4/2004 |
| JP | 2004-346172 | 12/2004 |
| JP | 2005-053820 | 3/2005 |
| JP | 2005-194658 | 7/2005 |
| JP | 2006-218342 | 8/2006 |

OTHER PUBLICATIONS

International Search Report issued Feb. 17, 2009 in International (PCT) Application No. PCT/JP2008/073007.
M. Lombardero et al., "Conformational Stability of B Cell Epitopes on Group I and Group II Dermatophagoides spp. Allergens", The Journal of Immunology, vol. 144, pp. 1353-1360, Feb. 15, 1990.
Supplementary European Search Report dated Jun. 1, 2012 issued in EP Application No. 08863141.1.
M. Richter et al., "Studies on the Uptake of Ragweed Pollen Allergens by Polyaminostyrene", Canadian Journal of Biochemistry and Physiology, vol. 40, pp. 471-475, Jan. 1, 1962, XP008151967.
AlcoChemical, AlzoNobel: "Versa-TL Performance Polymers for Consumer and Industrial Cleaning Applications", Sep. 22, 2000, XP002676363.

* cited by examiner

*Primary Examiner* — Duane Smith
*Assistant Examiner* — Sonji Turner
(74) *Attorney, Agent, or Firm* — Wenderoth, Lind & Ponack, L.L.P.

(57) ABSTRACT

The present invention provides an allergen inhibitor which effectively prevents allergens from reacting with specific antibodies, mitigates the allergic symptoms or prevents appearance thereof, and is less likely to cause unpredictable discoloration and discoloration under usual conditions. The allergen inhibitor of the present invention comprises an allergen-inhibiting compound including a linear polymer having at least one of substituents represented by the formulas (1) to (3) at a side chain. Thus, the allergen inhibitor of the present invention shows excellent allergen-inhibiting effects.

22 Claims, No Drawings

ALLERGEN INHIBITOR, ALLERGEN-INHIBITING PRODUCT, ALLERGEN INHIBITING METHOD, AND USE AS ALLERGEN INHIBITOR

TECHNICAL FIELD

The present invention relates to an allergen inhibitor which prevents allergens, such as pollen of plants (e.g. *Cryptomeria japonica*), Acari and house dust, from reacting with specific antibodies and is less likely to cause unpredictable discoloration and discoloration under usual conditions; an allergen-inhibiting product obtained by application of the allergen inhibitor to an allergen target article; a method for inhibiting an allergen with using the allergen-inhibiting compound; and use as an allergen inhibitor.

BACKGROUND ART

These days, various allergic diseases such as atopic dermatitis, bronchial asthma and allergic rhinitis have become a problem. Such allergic diseases is mainly caused by an increase in the amounts of allergens in the living space, such as allergens of Acari in houses, especially those of *Dermatophagoides* (Der 1, Der 2) abundantly existing in house dust and allergens of *Cryptomeria japonica* pollens (Cry j1, Cry j2) abundantly floating in the air mainly in the spring.

Here, *Dermatophagoides* itself does not serve as allergens but the dead bodies and excrement of *Dermatophagoides* serve as allergens. Thus, eradication of *Dermatophagoides* with an acaricide does not a fundamental solution for allergic diseases. On the contrary, the eradication of *Dermatophagoides* causes an increase in the number of the dead bodies, and thus may worsen allergic conditions.

The allergens of *Cryptomeria japonica* pollens Cry j1 and Cry j2 are a glycoprotein with a molecular weight of about 40 kDa and a glycoprotein with a molecular weight of about 37 kDa, respectively. The allergens of *Cryptomeria japonica* which is attached to the nasal mucosa and the like mucosae are recognized as foreign matter and cause inflammatory reactions.

In order to mitigate allergic symptoms or prevent new allergic symptoms, it is required to perfectly remove allergens from the living space or inactivate allergens by treatments such as denaturalization thereof.

Since allergens are proteins, allergens denaturalized by heat, strong acids, strong bases or other factors presumably lose their allergenic activities. Allergens have very high stability, however, and are not easily denaturalized by factors safely usable at home such as oxidants, reducing agents, heat, alkalis and acids (see Non-Patent Document 1).

In addition, the attempt to denaturalize the allergens contaminating target articles may cause damages on the target articles contaminated by the allergens according to the conditions. Examples of the target articles include tatami mats, carpets, floors, furniture (e.g. sofas, upholstered chairs and tables), bedclothes (e.g. beds, futons and sheets), articles used inside vehicles (e.g. seats and child restraint systems), interior materials for vehicles (e.g. ceiling materials), kitchen utensils, baby goods, curtains, wall papers, towels, clothes, stuffed toys, other textile products and air cleaners (including the bodies and the filters thereof).

Thus, there have been devised methods for chemically denaturalize the surfaces of allergen molecules under relatively mild conditions. For example, there are proposed a method for inhibiting allergens with tannic acid that is used for tanning rawhides (Patent Document 1); a method for inhibiting allergens with tea extracts or the like substances (Patent Document 2); and a method for inhibiting allergens with hydroxy benzoic acid-type compounds or salts thereof (Patent Document 3). Allergen-inhibiting effects are confirmed in these methods.

Here, most compounds used in these methods are a type of polyphenols, and each has a color. Thus, these compounds disadvantageously color the target articles.

Patent Document 4 proposes a method for inhibiting allergens with aromatic hydroxy compounds, which provides improvement in the problem of coloring the target articles. In the case of treating a target article having a light color such as white, however, coloring may occur and the improvement effects are insufficient.

Non-Patent Document 1: The journal of Immunology Vol. 144, 1353-1360
Patent Document 1: Japanese Kokai Publication S61-44821 (JP-A S61-44821)
Patent Document 2: Japanese Kokai Publication H06-279273 (JP-A H06-279273)
Patent Document 3: Japanese Kokai Publication H11-292714 (JP-A H11-292714)
Patent Document 4: Japanese Kokai Publication 2003-81727 (JP-A 2003-81727)

DISCLOSURE OF THE INVENTION

Problems to be Solved by the Invention

The present invention provides an allergen inhibitor which effectively prevents allergens from reacting with specific antibodies, mitigates the allergic symptoms or prevents appearance thereof, and is less likely to cause unpredictable discoloration and discoloration under usual conditions; an allergen-inhibiting product obtained by application of the allergen inhibitor to an allergen target article; a method for inhibiting an allergen with the allergen-inhibiting compound; and use as an allergen inhibitor.

Means for Solving the Problems

One aspect of the present invention relates to an allergen inhibitor comprising a compound including a linear polymer having at least one of substituents at a side chain, the substituents represented by the formulas (1) to (3).

[Chem. 1]

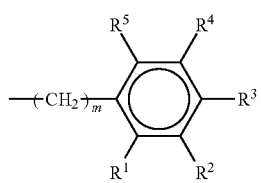

Formula(1)

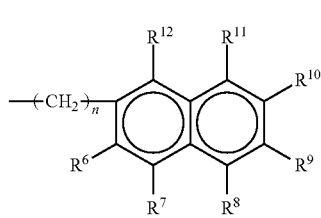

Formula(2)

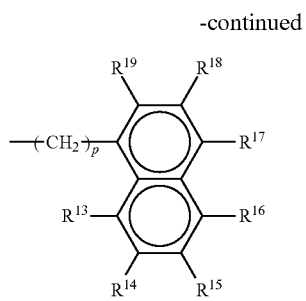
Formula(3)

Here, the term "allergen inhibitor" means one having allergen-inhibiting effects. The term "allergen-inhibiting effects" means the effects of denaturalizing or adsorbing allergens, such as allergens of *Dermatophagoides* (Der1 and Der2), allergens of pollen of *Cryptomeria japonica* (Cryj1 and Cryj2) floating in the air and allergens from dogs and cats (Can f1 and Fel d1), to inhibit reactivity of the allergens to specific antibodies. Such allergen-inhibiting effects may be determined by, for example, a method in which the amounts of allergens are measured by the ELISA method with an ELISA kit commercially available from NichiNichi Pharmaceutical, Co., Ltd. and a method in which allergenicity is evaluated by using an allergen-measuring apparatus (Mitey Checker from Sumika Enviro-Science Co., Ltd.).

In the formulas (1) to (3), m, n and p each represent an integer of 0 to 2. when m, n and p each are 3 or higher, the allergen-inhibiting compound tends to lose its allergen-inhibiting effects.

In the formula (1), $R^1$ to $R^5$ each are hydrogen (—H), a carboxyl group (—COOH), a sulfonic group (—$SO_2$H), an amino group (—$NH_2$), a derivative of a carboxyl group (—COOH), a derivative of a sulfonic group (—$SO_2$H), or a derivative of an amino group (—$NH_2$). At least one of $R^1$ to $R^5$ is required to be a carboxyl group (—COOH), a sulfonic group (—$SO_2$H), an amino group (—$NH_2$), a derivative of a carboxyl group (—COOH), a derivative of a sulfonic group (—$SO_2$H), or a derivative of an amino group (—$NH_2$).

Similarly, in the formula (2), $R^6$ to $R^{12}$ each are hydrogen (—H), a carboxyl group (—COOH), a sulfonic group (—$SO_2$H), an amino group (—$NH_2$), a derivative of a carboxyl group (—COOH), a derivative of a sulfonic group (—$SO_2$H), or a derivative of an amino group (—$NH_2$). At least one of $R^6$ to $R^{12}$ is required to be a carboxyl group (—COOH), a sulfonic group (—$SO_3$H), an amino group (—$NH_2$), a derivative of a carboxyl group (—COOH), a derivative of a sulfonic group (—$SO_2$H), or a derivative of an amino group (—$NH_2$).

In addition, in the formula (3), $R^{13}$ to $R^{19}$ each are hydrogen (—H), a carboxyl group (—COOH), a sulfonic group (—$SO_3$H), an amino group (—$NH_2$), a derivative of a carboxyl group (—COOH), a derivative of a sulfonic group (—$SO_3$H), or a derivative of an amino group (—$NH_2$). At least one of $R^{13}$ to $R^{19}$ is required to be a carboxyl group (—COOH), a sulfonic group (—$SO_3$H), an amino group (—$NH_2$), a derivative of a carboxyl group (—COOH), a derivative of a sulfonic group (—$SO_2$H), or a derivative of an amino group (—$NH_2$).

When each of the substituent represented by the formulas (1) to (3) does not have a carboxyl group, a sulfonic group, an amino group or derivatives thereof as a substituent, the allergen inhibitor does not show its allergen inhibiting effects.

Examples of the derivative of a carboxyl group include —$COOCH_2$, —$COOC_2H_5$ and salts of a carboxyl group. Examples of the salts of a carboxyl group include —COONa and (—COO)$_2$Ca.

Examples of the derivative of a sulfonic group include —$SO_2CH_2$, —$SO_2C_2H_5$ and salts of a sulfonic group. Examples of the salts of a sulfonic group include —SO Na, (—$SO_3$)$_2$Ca and —$SO_2$ $NH_4^+$.

Examples of the derivative of an amino group include —$NHCH_2$, —$NHC_2H_5$, —$NHCOCH_3$ and salts of an amino group. Examples of the salts of an amino group include —$NH_2$.HCl.

In the formula (1), the total number of carboxyl groups, sulfonic groups, amino groups and derivatives thereof is preferably 1 to 3, and more preferably 1. This is because a large number thereof causes lost of the allergen-inhibiting effects.

In addition, it is preferable that $R^3$ is a carboxyl group, a sulfonic group, an amino group or a derivative thereof, and that $R^1$, $R^2$, $R^4$ and $R^5$ each are hydrogen in the formula (1). This is because such a structure less causes steric hindrance.

The linear polymer having the substituents represented by the formulas (1) to (3) at a side chain is not particularly limited. Preferable examples thereof include vinyl polymers, polyesters and polyamides. The linear polymer may be coupled with the substituents represented by the formulas (1) to (3) via any chemical bond such as a carbon-carbon bond, an ester bond, an ether bond or an amide bond.

The allergen-inhibiting compound having at least one of the substituents represented by the formulas (1) to (3) at a side chain of the linear polymer is preferably a sulfonic acid salt of a polymer containing a styrene sulfonic acid component; a polymer containing a styrene sulfonic acid derivative component; a copolymer containing a styrene sulfonic acid salt component and a styrene sulfonic acid derivative component other than the styrene sulfonic acid salt component; a sulfonic acid derivative of a compound formed by sulfonation of polystyrene; or a sulfonic acid derivative of a compound formed by sulfonation of a polymer containing a styrene component.

The sulfonic acid salt of a polymer containing a styrene sulfonic acid component is not particularly limited. It is preferably a sulfonic acid sodium salt of a polymer containing a styrene sulfonic acid component; a sulfonic acid calcium salt of a polymer containing a styrene sulfonic acid component; a sulfonic acid ammonium salt of a polymer containing a styrene sulfonic acid component; a sulfonic acid magnesium salt of a polymer containing a styrene sulfonic acid component; or a sulfonic acid barium salt of a polymer containing a styrene sulfonic acid component. It is more preferably a sulfonic acid sodium salt of a homopolymer of styrene sulfonic acid. It is particularly preferably a sulfonic acid sodium salt of a homopolymer of p-styrene sulfonic acid. It is most preferably a homopolymer of sodium p-styrene sulfonate. The polymer containing a styrene sulfonic acid derivative component is not particularly limited, and is preferably a polymer of ethyl styrene sulfonate.

The sulfonic acid derivative of a compound formed by sulfonation of polystyrene is preferably a sulfonic acid sodium salt of a compound formed by sulfonation of polystyrene; a sulfonic acid calcium salt of a compound formed by sulfonation of polystyrene; a sulfonic acid ammonium salt of a compound formed by sulfonation of polystyrene; a sulfonic acid magnesium salt of a compound formed by sulfonation of polystyrene; a sulfonic acid barium salt of a compound formed by sulfonation of polystyrene; or a sulfonic acid ethyl ester of a compound formed by sulfonation of polystyrene. It is preferably a sulfonic acid sodium salt of a compound formed by sulfonation of polystyrene.

The sulfonic acid derivative of a compound formed by sulfonation of a polymer containing a styrene component is preferably a sulfonic acid sodium salt of a compound formed by sulfonation of a polymer containing a styrene component;

a sulfonic acid calcium salt of a compound formed by sulfonation of a polymer containing a styrene component; a sulfonic acid ammonium salt of a compound formed by sulfonation of a polymer containing a styrene component; a sulfonic acid magnesium salt of a compound formed by sulfonation of a polymer containing a styrene component; or a sulfonic acid barium salt of a compound formed by sulfonation of a polymer containing a styrene component. It is preferably a sulfonic acid sodium salt of a compound formed by sulfonation of a polymer containing a styrene component or a sulfonic acid ethyl ester of a compound formed by sulfonation of a polymer containing a styrene component.

The polymer containing a styrene component or the polystyrene preferably has a sulfonation ratio of preferably 5 to 100 mol %, and more preferably 10 to 100 mol %. A sulfonation ratio of lower than 5 mol % is apt to decrease the allergen-inhibiting effects of the allergen-inhibiting compound. The sulfonation ratio of the polymer containing a styrene component or the polystyrene may be measured by a known method, for example, a method in which a ratio of the numbers of carbon atoms and sulfur atoms is measured by elementary analysis; and a method in which the amount of bound sulfuric acid is measured (JIS K3362:1998, determination of anionic surfactant, corresponding ISO is 2271). The sulfonation ratio indicates a ratio of structural monomers into which a sulfonic group is introduced among the monomer components having the substituents represented by the formulas (1) to (3). In the case of a compound formed by sulfonation of the polystyrene, the sulfonation ratio of 100 mol % means that every benzene ring in the polystyrene has one sulfonic group introduced thereinto.

In the polymer containing a styrene component, examples of the monomer components other than the styrene component include alkyl acrylates, alkyl methacrylates, vinyl alkyl ethers, vinyl acetate, ethylene, propylene, butylene, butadiene, diisobutylene, vinyl chloride, vinylidene chloride, 2-vinyl naphthalene, styrene, acrylonitrile, acrylic acid, sodium acrylate, methacrylic acid, maleic acid, fumaric acid, maleic anhydride, acrylamide, methacrylamide, diacetone acrylamide, vinyl toluene, xylene sulfonic acid, vinylpyridine, vinyl sulfonic acid, vinyl alcohol, methyl methacrylate, sodium methacrylate and hydroxyethyl methacrylate.

Sulfonation of the polymer containing a styrene component or the polystyrene may be performed by a known technique. Examples thereof include a method using substances such as sulfur trioxide or concentrated sulfuric acid. The sulfonic acid derivative of a compound formed by sulfonation of the polymer containing a styrene component or the polystyrene may be produced by, for example, a method including: sulfonating the polymer containing a styrene component or the polystyrene; and then neutralizing a dispersion containing the sulfonated compound with an alkaline aqueous solution. Examples of the alkaline aqueous solution include sodium hydroxide and potassium hydroxide.

The allergen-inhibiting compound is preferably a compound formed by polymerization or copolymerization of monomers having the substituents represented by the formulas (1) to (3). Examples of the monomers include p-styrene sulfonic acid, m-styrene sulfonic acid, o-styrene sulfonic acid, sodium p-styrene sulfonate, sodium m-styrene sulfonate, sodium o-styrene sulfonate, calcium p-styrene sulfonate, calcium m-styrene sulfonate, calcium o-styrene sulfonate, ammonium p-styrene sulfonate, ammonium m-styrene sulfonate, ammonium o-styrene sulfonate, magnesium p-styrene sulfonate, magnesium m-styrene sulfonate, magnesium o-styrene sulfonate, barium p-styrene sulfonate, barium m-styrene sulfonate, barium o-styrene sulfonate, ethyl p-styrene sulfonate, ethyl m-styrene sulfonate, ethyl o-styrene sulfonate, 4-vinyl benzoic acid, sodium 4-vinyl benzoate, methyl 4-vinyl benzoate, 4-vinylaniline, amino styrene hydrochloric acid salt, N-acetyl aminostyrene, N-benzoyl aminostyrene, naphthalene sulfonic acid, sodium naphthalene sulfonate and calcium naphthalene sulfonate. Preferably used is sodium styrene sulfonate. More preferably used is sodium p-styrene sulfonate (sodium 4-styrene sulfonate) because it less causes steric hindrance in reactivity with allergens.

The sulfonic acid salt of a polymer containing a styrene sulfonic acid component may be produced by a known method. Examples of the production method include a method in which a styrene sulfonic acid salt is radically polymerized; and a method in which sulfonic acid of a homopolymer of styrene sulfonic acid is neutralized with alkali such as sodium hydroxide, calcium hydroxide, potassium hydroxide, or ammonium hydroxide.

In the molecule of the sulfonic acid salt of a polymer containing a styrene sulfonic acid component, not all of the sulfonic groups are required to be a salt; when the ratio of sulfonic groups converted into salts is too low, however, the allergen inhibitor is apt to have high acidity which causes damages to the below-mentioned allergen target article. Thus, the ratio is preferably 50 mol % or more, more preferably 70 to 100 mol %, and particularly preferably 85 to 100 mol %.

The ratio of sulfonic groups converted into salts in the molecule of the sulfonic acid salt of a polymer containing a styrene sulfonic acid component is determined as follows.

In the case that the sulfonic acid salt of a polymer containing a styrene sulfonic acid component is obtained by polymerization of a monomer containing a styrene sulfonic acid salt, calculate the total number of moles of the sulfonic groups and the derivatives thereof in the monomer used in the polymerization and the number of moles of sulfonic groups converted into salts; and then calculate the percentage of the number of moles of the sulfonic groups converted into salts to the total number of moles.

In the case that a homopolymer of styrene sulfonic acid is prepared by polymerization of styrene sulfonic acid as a monomer, and then this homopolymer of styrene sulfonic acid is neutralized with alkali to produce a sulfonic acid salt of the homopolymer of styrene sulfonic acid, measure the number of moles of consumed alkali by neutralization titration and the number of moles of styrene sulfonic acid used in the polymerization, and then calculate the percentage of the number of moles of the consumed alkali to the number of moles of the styrene sulfonic acid.

A lower Z average molecular weight (Mz) of the sulfonic acid salt of a homopolymer of styrene sulfonic acid tends to decrease the allergen-inhibiting effects. Thus, the Mz is preferably 150,000 or more, more preferably 200,000 or more, and particularly preferably 500,000 or more. In contrast, a too high Mz thereof tends to decrease handleability of the allergen inhibitor. Thus, the upper limit of the Mz is preferably 5,000,000.

The weight average molecular weight and the Z average molecular weight of a polymer herein mean those measured by size exclusion chromatography using polyethylene oxide as a standard substance. The weight average molecular weight and the Z average molecular weight of a polymer may be measured under the following conditions, for example;

Column: (two pieces of TSKgel GMPWXL 7.8 mm I.D.× 30 cm, produced by TOSOH Corp.)

Eluting solvent: (0.2 M aqueous sodium sulfate: acetonitrile=9:1)

Flow rate: 1 mL/min
Temperature: 40° C.
Detection: UV (210 nm)
Standard polyethylene oxide: (7 types of SE-2, -5, -8, -15, -30, -70 and -150, produced by TOSOH Corp.)

The allergen-inhibiting compound may be a copolymer of a monomer having the substituents represented by the formulas (1) to (3) and a monomer copolymerizable therewith. Such a copolymer may be a random copolymer or a block copolymer, and is preferably a block copolymer.

In the case that the allergen-inhibiting compound is a copolymer of a monomer having the substituents represented by the formulas (1) to (3) and a monomer copolymerizable therewith, the degree of polymerization at block portions derived from the monomer having the substituents represented by the formulas (1) to (3) is preferably 5 to 6,000. When the degree of polymerization is too low, the allergen inhibitor loses its allergen-inhibiting effects. On the other hand, the higher degree of polymerization tends to decrease handling capability of the allergen inhibitor.

In the case that the allergen-inhibiting compound is a copolymer of a monomer having the substituents represented by the formulas (1) to (3) and a monomer copolymerizable therewith, the amount of the monomer component having the substituents represented by the formulas (1) to (3) in the copolymer is preferably 5% by weight or more, more preferably 10% by weight or more, and particularly preferably 15 to 95% by weight. When an amount of the monomer component having the substituents represented by the formulas (1) to (3) is too low, the allergen inhibitor does not tend to show its allergen-inhibiting effects.

Examples of the monomer copolymerizable with the monomer having the substituents represented by the formulas (1) to (3) include alkyl acrylates, alkyl methacrylates, vinyl alkyl ethers, vinyl acetate, ethylene, propylene, butylene, butadiene, diisobutylene, vinyl chloride, vinylidene chloride, 2-vinyl naphthalene, styrene, acrylonitrile, acrylic acid, sodium acrylate, methacrylic acid, maleic acid, fumaric acid, maleic anhydride, acrylamide, methacrylamide, diacetone acrylamide, vinyl toluene, xylene sulfonic acid, vinylpyridine, vinyl sulfonic acid, vinyl alcohol, methyl methacrylate, sodium methacrylate and hydroxyethyl methacrylate.

Preferably used as the monomer copolymerizable with the monomer having the substituents represented by the formulas (1) to (3) are styrene, vinyl toluene and 2-vinyl naphthalene, and more preferably used is styrene.

With respect to the weight average molecular weights of the polymer formed by polymerization or copolymerization of the monomers having the substituents represented by the formulas (1) to (3) and of the copolymer of the monomer having the substituents represented by the formulas (1) to (3) and the monomer copolymerizable therewith, a lower value is apt to lose the allergen-inhibiting effects of the allergen-inhibiting compound, while a higher value is apt to decrease handling capability of the allergen inhibitor. Thus, in the case of the polymer formed by homopolymerization of the monomer having the substituents represented by the formulas (1) to (3), the weight average molecular weight is preferably 200,000 to 5,000,000. In the case of the polymer formed by copolymerization of the monomers each having the substituents represented by the formulas (1) to (3) and the copolymer of the monomer having the substituents represented by the formulas (1) to (3) and the monomer copolymerizable therewith, the weight average molecular weight is preferably 5,000 to 5,000,000, and more preferably 5,000 to 2,000,000.

The weight average molecular weight (Mw) of the sulfonic acid derivative of a compound formed by sulfonation of polystyrene or the sulfonic acid derivative of a compound formed by sulfonation of a polymer containing a styrene component is preferably 5,000 to 5,000,000, and more preferably 5,000 to 2,000,000. When the weight average molecular weight is too low, the allergen inhibitor does not tend to show its allergen-inhibiting effects. On the other hand, a higher weight average molecular weight tends to decrease handling capability of the allergen inhibitor.

The allergen-inhibiting compound may be soluble or insoluble in water. In the case that the allergen inhibitor is applied to the allergen target article which are required to have washing resistance, such as clothes and futons, the allergen-inhibiting compound is preferably insoluble in water. Here, the phrase "insoluble in water (water insolubility)" means that the amount in grams of the compound soluble in 100 g of water having pH of from 5 to 9 at 20° C. (hereinafter, referred to as "solubility") is 1 or less, and an allergen-inhibiting compound having a solubility exceeding 1 is referred to as "soluble in water".

An allergen-inhibiting compound insoluble in water is capable of preventing the allergen inhibitor from dissolving into water to disappear even when an allergen target article is touched with water. Thus, the allergen-inhibiting effects of the below-mentioned allergen-inhibiting products are stably maintained for a long time.

Examples of the method for imparting water insolubility to the allergen-inhibiting compound include a method in which a water-soluble allergen-inhibiting compound is impregnated with a curing agent and the allergen-inhibiting compound is cross-linked; and a method in which a water-soluble allergen-inhibiting compound is fixed on a carrier.

In the case that the allergen-inhibiting compound has a sulfonic group or a derivative thereof, examples of the method for imparting water insolubility to the allergen-inhibiting compound include a method in which a moiety of the compound is desulfonated; a method in which the structure of the sulfonic acid salt moiety is partially modified; and a method in which the compound is converted into a poorly water-soluble salt. In the case that the allergen-inhibiting compound is the sulfonic acid salt of a compound formed by sulfonation of polystyrene or the sulfonic acid derivative of a compound formed by sulfonation of polystyrene, examples of the method for imparting water insolubility to the allergen-inhibiting compound include a method in which the amount of sulfonic groups to be introduced into polystyrene is reduced.

Examples of the desulfonation method include a method in which the allergen-inhibiting compound is reacted with water vapor at high temperature. Examples of the method for modifying the structure of a sulfonic acid salt moiety include a method in which the allergen-inhibiting compound is melted in sodium hydroxide and then is converted into a phenol.

The curing agent of the allergen-inhibiting compound is not particularly limited as long as it is capable of cross-linking the allergen-inhibiting compound. Examples thereof include amine compounds; compounds synthesized from the amine compounds such as polyaminoamide compounds; tertiary amine compounds; imidazole compounds; hydrazide compounds; melamine compounds; acid anhydrides; phenol compounds; heat-latent cation polymerization catalysts; photo-latent cation polymerization initiators; dicyanamide and derivatives thereof; divinylbenzene; bis(vinylphenyl)ethane; and bis(vinylphenyl)sulfone. Each of these may be used alone, or two or more of these may be used in combination.

The amine compound is not particularly limited. Examples thereof include aliphatic amines such as ethylenediamine, diethylenetriamine, triethylenetetramine, tetraethylenepentamine, polyoxypropylenediamine and polyoxypropylenetriamine and derivatives thereof; alicyclic amines, such as menthenediamine, isophoronediamine, bis(4-amino-3-methylcyclohexyl)methane, diaminodicyclohexylmethane, bis(aminomethyl)cyclohexane, N-aminoethylpiperazine and 3,9-bis(3-aminopropyl)2,4,8,10-tetraoxaspiro(5,5)undecane and derivatives thereof; and aromatic amines such as m-xylenediamine, α-(m-aminophenyl)ethylamine, α-(p-aminophenyl)ethylamine, m-phenylenediamine, diaminodiphenylmethane, diaminodiphenylsulfone and α,α-bis(4-aminophenyl)-p-diisopropylbenzene and derivatives thereof.

The compound synthesized from the amine compound is not particularly limited. Examples thereof include polyaminoamide compounds synthesized from the amine compound with a carboxylic acid compound, such as succinic acid, adipic acid, azelaic acid, sebacic acid, dodecadioic acid, isophthalic acid, terephthalic acid, dihydroisophthalic acid, tetrahydroisophthalic acid, and hexahydroisophthalic acid and derivatives thereof; polyaminoimide compounds synthesized from the amine compound with a maleimide compound, such as diaminodiphenylmethane bismaleimide, and derivatives thereof; ketimine compounds synthesized from the amine compound with a ketone compound, and derivatives thereof; and polyamino compounds synthesized from the amine compound with a compound such as an epoxy compound, urea, thiourea, an aldehyde compound, a phenol compound and an acryl compound and derivatives thereof.

The tertiary amine compound is not particularly limited. Examples thereof include N,N-dimethylpiperazine, pyridine, picoline, benzyldimethylamine, 2-(dimethylaminomethyl) phenol, 2,4,6-tris(dimethylaminomethyl)phenol, 1,8-diazabiscyclo(5,4,0)-undecene-1 and derivatives thereof.

The imidazole compound is not particularly limited. Examples thereof include 2-methyl imidazole, 2-ethyl-4-methyl imidazole, 2-undecyl imidazole, 2-heptadecylimidazole, 2-phenyl imidazole and derivatives thereof.

The hydrazide compound is not particularly limited. Examples thereof include 1,3-bis(hydrazinocarboethyl)-5-isopropylhydantoin, 7,11-octadecadiene-1,18-dicarbohydrazide, eicosanedioic dihydrazide, dihydrazide adipate, and derivatives thereof.

The melamine compound is not particularly limited. Examples thereof include 2,4-diamino-6-vinyl-1,3,5-triadine and derivatives thereof.

The acid anhydride is not particularly limited. Examples thereof include phthalic anhydride, trimellitic anhydride, pyromellitic anhydride, benzophenonetetracarboxylic anhydrides, ethyleneglycol-bis(anhydrotrimellitate), glycerol tris (anhydrotrimellitate), methyl tetrahydrophthalic anhydride, tetrahydrophthalic anhydride, nadic anhydride, methylnadic anhydride, trialkyl tetrahydrophthalic anhydrides, hexahydrophthalic anhydride, methylhexahydrophthalic anhydride, 5-(2,5-dioxotetrahydrofuryl)-3-methyl-3-cyclohexene-1,2-dicarboxylic anhydrides, trialkyl tetrahydrophthalic anhydrides/maleic anhydride adducts, dodecenyl succinic anhydride, polyazelaic anhydride, polydodecanedioic anhydride, and chlorendic anhydride and derivatives thereof.

The phenol compound is not particularly limited. Examples thereof include phenol novolac, o-cresol novolac, p-cresol novolac, t-butyl phenol novolac, and dicyclopentadiene cresol, and derivatives thereof.

The heat-latent cation polymerization catalyst is not particularly limited. Examples thereof include ionic heat-latent cation polymerization catalysts, such as a benzylsulfonium salt, a benzyl ammonium salt, a benzyl pyridinium salt and a benzyl phosphonium salt, having a counter anion such as antimony hexafluoride, phosphor hexafluoride and boron tetrafluoride; and non-ionic heat-latent cation polymerization catalysts such as N-benzyl phthalimide and aromatic sulfonic acid esters.

The photo-latent cation polymerization initiator is not particularly limited. Examples thereof include ionic photo-latent cation polymerization initiators such as onium salts, e.g. aromatic diazonium salts, aromatic halonium salts and aromatic sulfonium salts, having a counter anion such as antimony hexafluoride, phosphor hexafluoride and boron tetrafluoride, and organic metal complexes such as iron-allene complexes, titanocene complexes and arylsilanol-aluminum complexes; and non-ionic photo-latent cation polymerization initiators such as nitrobenzyl esters, sulfonic acid derivatives, phosphoric acid esters, phenol sulfonic acid esters, diazonaphthoquinone and N-hydroxyimidosulfonate.

The carrier on which the allergen-inhibiting compound fixed is not particularly limited. Examples thereof include inorganic carriers such as talc, Bentonite, clay, kaolin, diatomite, silica, vermiculite, and pearlite, and organic polymeric carriers such as cross-linked agarose, polyethylene, and polypropylene.

The form of the organic polymeric carrier is not particularly limited. Examples thereof include a fine particulate form, a fibrous form, a sheet-like form, a film form and foam. In the case that the allergen-inhibiting compound is supported on foam, the allergen-inhibiting compound may be supported on a foamable molding which is a raw material of the foam before foaming, or may be supported on the foam after foaming.

The method for fixing the allergen-inhibiting compound on the carrier is not particularly limited. Examples thereof include a method in which the allergen-inhibiting compound is adsorbed on the carrier, and a method in which the allergen-inhibiting compound is fixed on the carrier by bonding such as chemical bonding (e.g. grafting), or bonding with a binder.

The allergen inhibitor of the present invention may be mixed with adjuvants for formulation such as a dispersant, an emulsifier, an antioxidant, an ultraviolet absorber and a migration inhibitor, as long as the allergen-inhibiting effects are not hindered. Further, the allergen inhibitor may contain agents such as an acaricide, a bactericide, a fungicide and a deodorant.

The migration inhibitor is not particularly limited. Examples thereof include salts such as calcium chloride, water-soluble cationic compounds, polyvinyl pyrrolidone, polyvinyl pyridine betaine and polyamine N-oxide polymers.

The following will describe instructions for use of the allergen inhibitor. The allergen inhibitor may be used in a general form such as a spray form, an aerosol form, a smoking form, thermal evaporation form and a mixed form in matrix.

The allergen inhibitor is formulated into a spray form through the following processes: the allergen inhibitor is dissolved or dispersed in a solvent to prepare a solution of the allergen inhibitor; and then agents such as a water-soluble chemical, an oil solution, an emulsion, and a suspension are mixed into the solution of the allergen inhibitor. Here, the term "spray form" represents a manner of use in which the solution of the allergen inhibitor under normal pressure is pressurized and thereby sprayed as mist.

Examples of the solvent include water (preferably, ion-exchange water), alcohols (e.g. methyl alcohol, ethyl alcohol, and propyl alcohol), hydrocarbons (e.g. toluene, xylene, methylnaphthalene, kerosene, and cyclohexane), ethers (e.g. diethyl ether, tetrahydrofuran and dioxane), ketones (e.g. acetone and methylethyl ketone) and amides (e.g. N,N-dimethyl formamide).

The allergen inhibitor is formulated into an aerosol form by addition of a solid carrier (e.g. talc, bentonite, clay, kaolin, diatomite, silica, vermiculite and pearlite) to the allergen inhibitor in the spray form.

Here, the term "aerosol form" represents a manner of use in which the solution of the allergen inhibitor and a propellant are charged in a container with the propellant compressed, and the allergen inhibitor is sprayed as mist by the pressure of the propellant. Examples of the propellant include nitrogen, carbonic acid gas, dimethyl ether and LPG.

The allergen inhibitor is formulated into a smoking form by addition of agents such as an oxygen-feeding agent (e.g. potassium perchlorate, potassium nitrate, and potassium chlorate), a combustion agent (e.g. saccharides and starch), an exothermic adjuster (e.g. guanidine nitrate, nitroguanidine, and guanyl urea phosphate), and an assistant for decomposing an oxygen-feeding agent (e.g. potassium chloride, copper oxide, chromium oxide, iron oxide, and active carbon) to the allergen inhibitor in a spray form. Here, the term "smoking form" represents a manner of use in which the allergen inhibitor is formed into fine particulate matter to be smoke and then dispersed.

The matrix with which the allergen inhibitor is mixed is not particularly limited as long as it does not modify the allergen inhibitor. Examples thereof include polysaccharides and salts thereof, dextrin, gelatin, higher alcohols, fats and oils, higher fatty acids such as stearic acid, paraffins, liquid paraffins, white vaseline, hydrocarbon gel ointments, polyethylene glycol, polyvinyl alcohol, sodium polyacrylate, and various paints.

The allergen inhibitor may be sprayed, dispersed, applied, or fixed to articles where allergens exist or may exist in future, that is, articles in which allergens should be inhibited (hereinafter referred to as "allergen target article"), such as consumer products; thereby, the allergen target article may be used as allergen-inhibiting products. Thus, allergens in the allergen target article are inhibited. The allergen inhibitors may be used alone, or may be used in combination. Preferably, the allergen inhibitor is formed into a suspension and sprayed to the allergen target article because the allergen inhibitor has excellent stability in the case that the solution of the allergen inhibitor is blended with a suspending agent to be a suspension. Examples of the method for chemically or physically fixing the allergen inhibitor to the allergen target article include a method in which the below-mentioned allergen-inhibiting compound is chemically coupled with or physically fixed to fibers.

Examples of the allergen target article include consumer products which serve as hotbeds of allergens in the living space. Examples of the consumer products include tatami mats, carpets, furniture (e.g. sofas, foams inside sofas, upholstered chairs, and tables), bedclothes (e.g. beds, futons, filling materials in futons, down in down-filled futons, sheets, mattresses, cushions, and foams for these articles), articles used inside vehicles such as cars, airplanes, and ships, and interior materials for the vehicles (e.g. seats, child restraint systems, and foams for these articles), kitchen utensils, baby goods, interior materials for buildings (e.g. wall papers and floor materials), textile products (e.g. curtains, towels, clothes, and stuffed toys), filters such as screen doors, drugs, quasi-drugs and cosmetics.

In particular, the allergen inhibitor of the present invention is suitable for applications in which color fading or discoloration due to light generally occurs because it hardly causes unexpected discoloration and discoloration due to usual living environments. Examples of such applications include interior materials for buildings, articles used inside vehicles, interior materials for vehicles, filters and textile products.

The filters are ones capable of isolating, filtrating, or removing foreign matter. Examples thereof include filters of devices such as air purifiers, air conditioners, cleaners, and exhaust fans; masks for preventing entry of foreign matter such as dust and pollen; and shoji doors, and screen doors and mosquito nets for preventing entry of insects.

The drugs, quasi-drugs, and cosmetics are not particularly limited. Examples thereof include external preparations for skin, nasal sprays, eye drops, shampoos, bath additives, hair styling products, foundations, and face wash products.

The interior materials for buildings are not particularly limited. Examples thereof include floor materials, wall papers, ceiling materials, coatings, and waxes.

The textile products are not particularly limited. Examples thereof include bedclothes, carpets, curtains, towels, clothes, and stuffed toys.

The articles used inside vehicles and interior materials for vehicles are not particularly limited. Examples thereof include seats, child restraint systems, seat belts, car mats, seat covers, and carpets.

When a small amount of the allergen inhibitor of the present invention is applied to the allergen target article, the allergen inhibitor does not tend to show its allergen-inhibiting effects, whereas a large amount thereof tends to cause damages on the allergen target article; thus, the amount thereof based on 100 parts by weight of the allergen target article is preferably 0.001 to 100 parts by weight, more preferably 0.01 to 50 parts by weight, particularly preferably 0.02 to 30 parts by weight and most preferably 0.02 to 20 parts by weight.

Examples of the target allergens of the allergen inhibitor of the present invention include animal allergens, such as allergens of *Dermatophagoides* (Der1, Der2) and allergens of dogs and cats (Can f1, Fel d1), and plant allergens such as allergens of pollen of *Cryptomeria japonica* (Cryj1, Cryj2) floating in the air and pollens. With respect to animal allergens on which the allergen inhibitor has a particular effect, any of Acari allergens may be a target (Acari, living things categorized in Arthropoda/Arachnida/Acari, generally divided into seven subphyla: Notostigmata, including Opilioacaridae; Tetrastigmata, including Holothyridae; Metastigmata, including *Ixodes ovatus* and *Argas japonicus*; Mesostigmata, including *Ornithonyssus bacoti* and *Dermanyssus hirundinis*; Prostigmata, including *Cheyletus malaccensis* and *Tarsonemus granarius; Dermatophagoides*, including *Dermatophagoides farinae*; Astigmata, including *Tyrophagus putrescentiae*; and Cryptostigmata, including *Haplochthonius simplex* Willman and Cosmochthonius reticulates). In particular, the allergen inhibitor has a better effect on *Dermatophagoides* which exist in house dust, especially in bedclothes, and causes allergic diseases.

The above-mentioned use of the allergen inhibitor by applying, if necessary, the allergen inhibitor to the allergen target article inhibits reactivity to specific antibodies of allergens which exist in the allergen target article or will exist therein in the future.

The allergen inhibitor may be applied to fibers to prepare allergen-inhibiting fibers, and thereby the allergen-inhibiting effects are imparted to the fibers themselves. The consumer products produced by using the allergen-inhibiting fibers are capable of preliminarily having the allergen-inhibiting effects.

Examples of the method for applying the allergen inhibitor to fibers include a method in which the allergen inhibitor is chemically bound to or physically fixed to fibers. The fibers are not particularly limited as long as they are capable of containing the allergen inhibitor. Examples thereof include: synthetic fibers such as polyester fibers, nylon fibers, acrylic fibers, and polyolefin fibers; semi-synthetic fibers such as acetate fibers; regenerated fibers such as cupra and rayon; natural fibers such as cotton, linen and ramie, wool, and silk; composite fibers thereof; and cotton blending.

Examples of the method for chemically fixing the allergen inhibitor to fibers include the allergen inhibitor is chemically bound to fibers by a grafting process. The grafting process is not particularly limited. Examples thereof include:

(1) graft polymerization method in which a polymerization initiating point is formed on a backbone polymer which is to be a fiber and the allergen inhibitor is grafted thereto as a branch polymer; and (2) a polymeric reaction method in which the allergen inhibitor is chemically bound to the fibers by polymeric reaction.

Examples of the graft polymerization include the following methods:

(1) radicals are generated and polymerized by chain transfer reaction to the fibers;

(2) an oxidation-reduction (redox) system is formed by the action of reducing substances such as alcohols, thiols and amines with substances such as ceric salts and silver sulfate, and free radicals are generated on the fibers and polymerized;

(3) the fibers are made to coexist with monomers which are materials of the allergen-inhibiting compound, and the fibers are irradiated with a radiation such as γ-rays or an accelerated electron beam;

(4) only the fibers are irradiated with a radiation such as γ-rays or an accelerated electron beam, then the fibers are mixed with monomers which are materials of the allergen-inhibiting compound, and polymerization occurs;

(5) polymers which constitute the fibers are oxidized and thus a peroxy group is introduced or a diazo group is introduced from an amino group at a side chain, and polymerization occurs with the introduced moiety serving as the polymerization starting point; and (6) a polymerization starting reaction of substances such as epoxy, lactum, and polar vinyl monomers is utilized which is due to active groups at the side chain such as a hydroxy group, an amino group, and a carboxyl group.

Specific graft polymerization methods are listed below:

(a) cellulose is triturated in a monomer which is a material of the allergen-inhibiting compound to yield free radicals, thereby triggering graft polymerization;

(b) graft polymerization is triggered by the use of a monomer which is a material of the allergen-inhibiting compound and a cellulose derivative (such as mercaptoethyl cellulose) as fibers having a group toward which chain transfer is likely to occur;

(c) a substance such as ozone or a peroxide is oxidized to yield radicals, thereby triggering graft polymerization;

(d) the double bond of allyl ether, vinyl ether, or methacrylic ester is introduced in the side chain of cellulose, thereby triggering graft polymerization;

(e) a substance such as sodium anthraquinone-2,7-disulfonate is used as a photosensitizer and ultraviolet rays are applied to fibers, thereby triggering graft polymerization; and (f) fibers are wrapped around a cathode, a monomer which is a material of the allergen-inhibiting compound is added to dilute sulfuric acid, and an external voltage is applied thereto, thereby electrochemically triggering graft polymerization.

In view of the fact that the graft polymerization here is for fibers, the following methods are preferable:

(g) fibers coated with glycidyl methacrylate (GMA) and benzoyl peroxide are heated in a solution of a monomer which is a material of the allergen-inhibiting compound, thereby triggering graft polymerization; and (h) a monomer which is a material of the allergen-inhibiting compound is added to a solution with benzoyl peroxide, a surfactant (nonionic surfactant or anionic surfactant), and monochloro benzene dispersed in water, and fibers such as polyester fibers are immersed therein and heated, thereby triggering graft polymerization.

The polymer reaction may be general reactions. Examples thereof include:

(1) chain transfer, oxidation and substitution to C—H;

(2) addition and oxidation to a double bond;

(3) esterification, etherification, and acetalization of a hydroxy group, substitution, addition, and hydrolysis to a group such as an ester group or an amido group, and substitution and elimination to a halogen group; and (4) substitution to an aromatic ring (halogenation, nitration, sulfonation, and chloromethylation).

The following will describe the method for physically fixing the allergen inhibitor to fibers. Examples of the method for physically fixing the allergen inhibitor to fibers include the following methods:

(1) the allergen inhibitor is dissolved or dispersed in a solvent to prepare a solution of the allergen inhibitor, and then fibers are immersed in the solution of the allergen inhibitor to impregnate the fiber with the solution of the allergen inhibitor;

(2) the solution of the allergen inhibitor is applied or splayed to the surface of fibers;

(3) fibers are immersed in a binder with the allergen inhibitor dissolved or dispersed therein, and the allergen inhibitor is fixed to the fibers via the binder; and (4) a binder with the allergen inhibitor dissolved or dispersed therein is applied or sprayed to the surface of fibers, and the allergen inhibitor is fixed to the fibers via the binder.

In the methods (1) and (2), the solution of the allergen inhibitor may contain the below-mentioned binder.

The solvent is not particularly limited. Examples thereof include: water; alcohols such as methyl alcohol, ethyl alcohol, and propyl alcohol; hydrocarbons such as toluene, xylene, methyl naphthalene, kerosene, and cyclohexane; ethers such as diethyl ether, tetrahydrofuran, and dioxane; ketones such as acetone and methylethyl ketone; and amides such as N,N-dimethyl formamide.

The binder is not particularly limited as long as it fixes the allergen inhibitor to the surface of fibers. Examples of binders produced from synthetic resin include urethane resins such as one pack-type urethane resin and two pack-type urethane resin, silicone resins, acryl resins, urethane acrylate resins, polyester resins, unsaturated polyester resins, alkyd resins, vinyl acetate resin, vinyl chloride resin, epoxy resins, and epoxy acrylate resins. Preferable among these are urethane resins.

The aforementioned description shows the methods in which the allergen inhibitor is chemically bound or physically fixed to separately prepared fibers; fibers may be produced by spinning of a fiber material with the allergen inhibitor chemically bound thereto.

The method for preparing a fiber material with the allergen inhibitor chemically bound thereto is not particularly limited. Examples thereof include a method in which a monomer having the substituents represented by the formulas (1) to (3) and a monomer which is to be a common fiber material are copolymerized to form a fiber material.

Effects of the Invention

The allergen inhibitor of the present invention contains the allergen-inhibiting compound which includes a linear polymer having at least one of the substituents represented by the formulas (1) to (3) at a side chain. Thus, it effectively prevents allergens from reacting with specific antibodies and reduces allergic symptoms or prevents appearance thereof. In addition, the allergen inhibitor is less likely to cause unexpected discoloration and discoloration under usual conditions; thus, it is suitably used for various consumer products.

BEST MODE FOR CARRYING OUT THE INVENTION

The following will more specifically describe the aspects of the present invention referring to examples; the present invention is not limited to these examples.

Example 1

40 parts by weight of an aqueous solution containing a homopolymer of sodium p-styrene sulfonate, which serves as the allergen-inhibiting compound, (trade name: PS-1, produced by Tosoh Organic Chemical Co., Ltd., amount of homopolymer of sodium p-styrene sulfonate: 20% by weight, weight average molecular weight (Mw): 25,000, Z average molecular weight (Mz): 49,000) was added to 60 parts by weight of ion-exchanged water, and they were uniformly mixed to give a solution of the allergen inhibitor. Here, the homopolymer of sodium p-styrene sulfonate was soluble in water. The ratio of sulfonic groups converted into sodium salts in the homopolymer of sodium p-styrene sulfonate was 100 mol %.

Example 2

Except that 40 parts by weight of an aqueous solution containing a homopolymer of sodium p-styrene sulfonate (trade name: PS-5, produced by Tosoh Organic Chemical Co., Ltd., amount of homopolymer of sodium p-styrene sulfonate: 20% by weight, weight average molecular weight (Mw): 109,000, Z average molecular weight (Mz): 200,000) was used as the allergen-inhibiting compound, a solution of the allergen inhibitor was prepared in the same manner as in Example 1. Here, the homopolymer of sodium p-styrene sulfonate was soluble in water. The ratio of sulfonic groups converted into sodium salts in the homopolymer of sodium p-styrene sulfonate was 100 mol %.

Example 3

Except that 40 parts by weight of an aqueous solution containing a homopolymer of sodium p-styrene sulfonate (trade name: PS-50, produced by Tosoh Organic Chemical Co., Ltd., amount of homopolymer of sodium p-styrene sulfonate: 20% by weight, weight average molecular weight (Mw): 390,000, Z average molecular weight (Mz): 618,000) was used as the allergen-inhibiting compound, a solution of the allergen inhibitor was prepared in the same manner as in Example 1. Here, the homopolymer of sodium p-styrene sulfonate was soluble in water. The ratio of sulfonic groups converted into sodium salts in the homopolymer of sodium p-styrene sulfonate was 100 mol %.

Example 4

Except that 40 parts by weight of an aqueous solution containing a homopolymer of sodium p-styrene sulfonate (trade name: PS-100, produced by Tosoh Organic Chemical Co., Ltd., amount of homopolymer of sodium p-styrene sulfonate: 20% by weight, weight average molecular weight (Mw): 529,000, Z average molecular weight (Mz): 758,000) was used as the allergen-inhibiting compound, a solution of the allergen inhibitor was prepared in the same manner as in Example 1. Here, the homopolymer of sodium p-styrene sulfonate was soluble in water. The ratio of sulfonic groups converted into sodium salts in the homopolymer of sodium p-styrene sulfonate was 100 mol %.

Example 5

Except that 40 parts by weight of an aqueous solution containing a homopolymer of sodium p-styrene sulfonate (trade name: PS-35, produced by Tosoh Organic Chemical Co., Ltd., amount of homopolymer of sodium p-styrene sulfonate: 20% by weight, weight average molecular weight (Mw): 386,000, Z average molecular weight (Mz): 588,000) was used as the allergen-inhibiting compound, a solution of the allergen inhibitor was prepared in the same manner as in Example 1. Here, the homopolymer of sodium p-styrene sulfonate was soluble in water. The ratio of sulfonic groups converted into sodium salts in the homopolymer of sodium p-styrene sulfonate was 100 mol %.

Example 6

Except that 40 parts by weight of an aqueous solution containing a random copolymer of sodium p-styrene sulfonate and sodium methacrylate (sodium p-styrene sulfonate content: 50% by weight, sodium methacrylate content: 50% by weight, amount of random copolymer of sodium p-styrene sulfonate and sodium methacrylate: 20% by weight, weight average molecular weight (Mw): 3,900) was used as the allergen-inhibiting compound, a solution of the allergen inhibitor was prepared in the same manner as in Example 1. Here, the random copolymer of sodium p-styrene sulfonate and sodium methacrylate was soluble in water. The ratio of sulfonic groups converted into sodium salts in the random copolymer of sodium p-styrene sulfonate and sodium methacrylate was 100 mol %.

Example 7

Except that 40 parts by weight of an aqueous solution containing a random copolymer of sodium p-styrene sulfonate and styrene (sodium p-styrene sulfonate content: 50% by weight, styrene content: 50% by weight, amount of random copolymer of sodium p-styrene sulfonate and styrene: 20% by weight, weight average molecular weight (Mw): 22,000) was used as the allergen-inhibiting compound, a solution of the allergen inhibitor was prepared in the same manner as in Example 1. Here, the random copolymer of sodium p-styrene sulfonate and styrene was soluble in water.

Example 8

280 parts by weight of sodium p-styrene sulfonate (produced by Wako Pure Chemical Industries, Ltd.) was dissolved in 645 parts by weight of water to give a monomer aqueous solution. Separately, 2.80 parts by weight of 2,2'-Azobis{2-methyl-N-[1,1'-bis(hydroxymethyl)-2-hydroxyethyl]propionamide} was dissolved in 60 parts by weight of water to give an aqueous solution of a polymerization initiator.

The atmosphere in a polymerization container was preliminarily substituted with nitrogen. 100 parts by weight of water was charged in the polymerization container and heated up to 85° C. under stirring. The monomer aqueous solution and the aqueous solution of the polymerization initiator were continuously supplied to the polymerization container over 6 hours so as to polymerize sodium p-styrene sulfonate.

After the supply of the monomer aqueous solution to the polymerization container was finished, the reactant in the container was matured over 2 hours. Thereby, a homopolymer of sodium p-styrene sulfonate was obtained. Here, the homopolymer of sodium p-styrene sulfonate had a weight average molecular weight of 298,000 and a Z average molecular weight of 477,000, and was soluble in water. The ratio of sulfonic groups converted into sodium salts in the homopolymer of sodium p-styrene sulfonate was 100 mol %.

The obtained homopolymer of sodium p-styrene sulfonate was dissolved in ion-exchanged water to give a solution of the allergen inhibitor with a concentration of the homopolymer of sodium p-styrene sulfonate of 8% by weight.

Example 9

280 parts by weight of sodium p-styrene sulfonate (produced by Wako Pure Chemical Industries, Ltd.) was dissolved in 645 parts by weight of water to give a monomer aqueous solution. Separately, 2.80 parts by weight of 4,4'-Azobis-(4-cyanopentaic sodium) was dissolved in 60 parts by weight of water to give an aqueous solution of a polymerization initiator.

The atmosphere in a polymerization container was preliminarily substituted with nitrogen. 100 parts by weight of water was charged in the polymerization container and heated up to 90° C. under stirring. The monomer aqueous solution and the aqueous solution of the polymerization initiator were continuously supplied to the polymerization container over 4 hours so as to polymerize sodium p-styrene sulfonate.

After the supply of the monomer aqueous solution to the polymerization container was finished, the mixture in the container was matured over 2 hours. Thereby, a homopolymer of sodium p-styrene sulfonate was obtained. Here, the homopolymer of p-styrene sulfonate had a weight average molecular weight of 314,000 and a Z average molecular weight of 515,000, and was soluble in water. The ratio of sulfonic groups converted into sodium salts in the homopolymer of sodium p-styrene sulfonate was 100 mol %.

The obtained homopolymer of sodium p-styrene sulfonate was dissolved in ion-exchanged water to give a solution of the allergen inhibitor with a concentration of the homopolymer of sodium p-styrene sulfonate of 8% by weight.

Example 10

280 parts by weight of sodium p-styrene sulfonate (produced by Wako Pure Chemical Industries, Ltd.) was dissolved in 645 parts by weight of water to give a monomer aqueous solution. Separately, 0.50 parts by weight of ammonium persulfate was dissolved in 40 parts by weight of water to give an aqueous solution of a polymerization initiator.

The atmosphere in a polymerization container was preliminarily substituted with nitrogen. 100 parts by weight of water was charged in the polymerization container and heated up to 85° C. under stirring. The monomer aqueous solution and the aqueous solution of the polymerization initiator were continuously supplied to the polymerization container over 4 hours so as to polymerize sodium p-styrene sulfonate.

After the supply of the monomer aqueous solution to the polymerization container was finished, the mixture in the container was matured over 2 hours. Thereby, a homopolymer of sodium p-styrene sulfonate was obtained. Here, the homopolymer of p-styrene sulfonate had a weight average molecular weight of 487,000 and a Z average molecular weight of 828,000, and was soluble in water. The ratio of sulfonic groups converted into sodium salts in the homopolymer of sodium p-styrene sulfonate was 100 mol %.

The obtained homopolymer of sodium p-styrene sulfonate was dissolved in ion-exchanged water to give a solution of the allergen inhibitor with a concentration of the homopolymer of sodium p-styrene sulfonate of 8% by weight.

Example 11

280 parts by weight of sodium p-styrene sulfonate (produced by Wako Pure Chemical Industries, Ltd.) was dissolved in 645 parts by weight of water to give a monomer aqueous solution. Separately, 2.80 parts by weight of ammonium persulfate was dissolved in 60 parts by weight of water to give an aqueous solution of a polymerization initiator.

The atmosphere in a polymerization container was preliminarily substituted with nitrogen. 100 parts by weight of water was charged in the polymerization container and heated up to 85° C. under stirring. The monomer aqueous solution and the aqueous solution of the polymerization initiator were continuously supplied to the polymerization container over 4 hours so as to polymerize of sodium p-styrene sulfonate.

After the supply of the monomer aqueous solution to the polymerization container was finished, the mixture in the container was matured over 2 hours. Thereby, a homopolymer of sodium p-styrene sulfonate was obtained. Here, the homopolymer of p-styrene sulfonate had a weight average molecular weight of 106,000 and a Z average molecular weight of 177,000, and was soluble in water. The ratio of sulfonic groups converted into sodium salts in the homopolymer of sodium p-styrene sulfonate was 100 mol %.

The obtained homopolymer of sodium p-styrene sulfonate was dissolved in ion-exchanged water to give a solution of the allergen inhibitor with a concentration of the homopolymer of sodium p-styrene sulfonate of 8% by weight.

Example 12

A sulfonic acid sodium salt of a compound formed by sulfonation of polystyrene (trade name: "VERSA-TL 502", produced by Akzo Nobel KK, sulfonation ratio: 99 mol % or more, weight average molecular weight: 685,000, Z average molecular weight: 1,153,000) serving as the allergen-inhibiting compound was dissolved in ion-exchanged water to give a solution of the allergen inhibitor with a concentration of the sulfonic acid sodium salt of a compound formed by sulfonation of polystyrene of 8% by weight. Here, the sulfonic acid sodium salt of a compound formed by sulfonation of polystyrene was soluble in water.

Example 13

An aqueous solution containing, as the allergen-inhibiting compound, a sulfonic acid ammonium salt of a compound formed by sulfonation of polystyrene (trade name: "VERSA-TL 125", produced by Akzo Nobel KK, amount of sulfonic acid ammonium salt of compound formed by sulfonation of polystyrene: 30% by weight, sulfonation ratio: 99 mol % or more, weight average molecular weight: 174,000, Z average molecular weight: 405,000) was added to ion-exchanged water to give a solution of the allergen inhibitor with a concentration of the sulfonic acid ammonium salt of a compound formed by sulfonation of polystyrene of 8% by weight. Here, the sulfonic acid ammonium salt of a compound formed by sulfonation of polystyrene was soluble in water.

Example 14

Except that 40 parts by weight of an aqueous solution containing a random copolymer of sodium p-styrene sulfonate and styrene (sodium p-styrene sulfonate content: 50% by weight, styrene content: 50% by weight, amount of random copolymer of sodium p-styrene sulfonate and styrene: 20% by weight, weight average molecular weight (Mw): 6,000) was used as the allergen-inhibiting compound, a solution of the allergen inhibitor was prepared in the same manner as in Example 1. Here, the random copolymer of sodium p-styrene sulfonate and styrene was soluble in water.

Example 15

Except that 40 parts by weight of an aqueous solution containing a random copolymer of sodium p-styrene sulfonate and styrene (sodium p-styrene sulfonate content: 40% by weight, styrene content: 60% by weight, amount of random copolymer of sodium p-styrene sulfonate and styrene: 20% by weight, weight average molecular weight (Mw): 6,000) was used as the allergen-inhibiting compound, a solution of the allergen inhibitor was prepared in the same manner as in Example 1. Here, the random copolymer of sodium p-styrene sulfonate and styrene was soluble in water.

Example 16

An aqueous solution of sodium hydroxide was added to an equivalent mole of p-vinyl benzoic acid (produced by Wako Pure Chemical Industries, Ltd.) to give sodium p-vinyl benzoate. Except that 280 parts by weight of sodium p-vinyl benzoate was used instead of sodium p-styrene sulfonate (produced by Wako Pure Chemical Industries, Ltd.), the same process as in Example 9 was performed to polymerize sodium p-vinyl benzoate and thus provide a homopolymer of sodium p-vinyl benzoate.

Here, the homopolymer of sodium p-vinyl benzoate had a weight average molecular weight of 293,000 and a Z average molecular weight of 467,000, and was soluble in water. The ratio of carboxyl groups converted into sodium salts in the homopolymer of sodium p-vinyl benzoate was 100 mol %.

The obtained homopolymer of sodium p-vinyl benzoate was dissolved in ion-exchanged water to give a solution of the allergen inhibitor with a concentration of the homopolymer of sodium p-vinyl benzoate of 8% by weight.

Example 17

Except that 280 parts by weight of lithium p-styrene sulfonate (produced by Tosoh Organic Chemical Co., Ltd.) was used instead of sodium p-styrene sulfonate (produced by Wako Pure Chemical Industries, Ltd.), the same process as in Example 10 was performed to provide a homopolymer of lithium p-styrene sulfonate. Here, the homopolymer of lithium p-styrene sulfonate had a weight average molecular weight of 329,000 and a Z average molecular weight of 521,000, and was soluble in water. The ratio of sulfonic groups regarded as lithium salts in the homopolymer of lithium p-styrene sulfonate was 100 mol %.

The obtained homopolymer of lithium p-styrene sulfonate was dissolved in ion-exchanged water to give an allergen inhibitor solution with a concentration of the homopolymer of lithium p-styrene sulfonate of 8% by weight.

Example 18

Except that 280 parts by weight of 4-vinylaniline (produced by Tokyo Chemical Industry Co., Ltd.) was used instead of sodium p-styrene sulfonate (produced by Wako Pure Chemical Industries, Ltd.), and a solution of water and ethanol in a weight ratio of 1:1 was used instead of water throughout the process, the same process as in Example 9 was performed to provide a homopolymer of p-vinylaniline. Here, the homopolymer of p-vinylaniline had a weight average molecular weight of 255,000 and a Z average molecular weight of 407,000, and was insoluble in water.

The obtained homopolymer of p-vinylaniline was suspended in ion-exchanged water to give a suspension of the allergen inhibitor with a concentration of the homopolymer of sodium p-styrene sulfonate of 8% by weight.

Example 19

Water and ethanol were mixed at a weight ratio of 1:1 to prepare a mixed solution. 98 parts by weight, of sodium p-styrene sulfonate (produced by Wako Pure Chemical Industries, Ltd.) and 42 parts by weight of styrene (produced by Wako Pure Chemical Industries, Ltd.) were dissolved in 645 parts by weight of the mixed solution to give a monomer aqueous solution. Separately, 0.50 parts by weight of 4,4'-azobis-(4-cyanopentaic sodium) was dissolved in 40 parts by weight of the mixed solution to give an aqueous solution of a polymerization initiator.

The atmosphere in a polymerization container was preliminarily substituted with nitrogen. 100 parts by weight of water was charged in the polymerization container and heated up to 75° C. under stirring. The monomer aqueous solution and the aqueous solution of the polymerization initiator were continuously supplied to the polymerization container over 6 hours so as to cause random copolymerization of styrene and sodium p-styrene sulfonate.

After the supply of the monomer aqueous solution to the polymerization container was finished, the mixture in the container was matured over 2 hours. Thereby, a random copolymer of styrene and sodium p-styrene sulfonate (styrene content: 70% by weight, sodium p-styrene sulfonate content: 30% by weight) was obtained. Here, the random copolymer of styrene and p-styrene sulfonate was insoluble in water.

The random copolymer of styrene and p-styrene sulfonate had a weight average molecular weight of 126,000. The ratio of sulfonic groups converted into sodium salts in the random copolymer of styrene and sodium p-styrene sulfonate was 100 mol %.

The obtained random copolymer of styrene and sodium p-styrene sulfonate was suspended in ion-exchanged water to give a suspension of the allergen inhibitor with a concentration of random copolymer of styrene and sodium p-styrene sulfonate of 8% by weight.

Example 20

3 mL of a suspension of a cross-linked agarose support (trade name: "Q Sepharose Fast Flow", produced by Pharmacia Corp.) was centrifuged for 5 minutes at 3,000 rpm. To the obtained sediment were added 0.5 mL of a random copolymer of sodium p-styrene sulfonate and styrene (sodium p-styrene sulfonate content: 50% by weight, styrene content: 50% by weight, amount of random copolymer of sodium p-styrene sulfonate and styrene: 20% by weight, weight average molecular weight (Mw): 22,000) as the allergen-inhibiting compound and 0.5 mL of ion-exchanged water. The mixture was sufficiently stirred and left standing for 24 hours to give a first suspension.

The first suspension was centrifuged for 5 minutes at 3,000 rpm. The supernatant of the first suspension was removed, and the residue thereof was collected. 3 mL of ion-exchanged water was added to the residue, and they were stirred to give a second suspension. The second suspension was centrifuged for 5 minutes at 3,000 rpm. The supernatant of the second suspension was removed, and the residue was collected.

The same process was further performed 4 times in which ion-exchanged water was added to the residue of the first suspension, they were stirred to give the second suspension, the second suspension was centrifuged, and the supernatant was removed and the residue was collected. Thereby, the residues were obtained.

Ion-exchanged water was added to the obtained residues so that the total volume was 3 mL to give a suspension of the allergen inhibitor adsorbed on the cross-linked agarose support.

Example 21

An allergen inhibitor containing, as the allergen-inhibiting compound, a sulfonic acid sodium salt of a compound formed by sulfonation of a copolymer of styrene and maleic acid (trade name: "VERSA-TL 3", produced by Akzo Nobel KK, styrene content: 75% by weight, maleic acid content: 25% by weight, sulfonation ratio of styrene: 99 mol % or more, weight average molecular weight (Mw): 20,000) was prepared. Here, the sulfonic acid sodium salt of a compound formed by sulfonation of a copolymer of styrene sulfonic acid and maleic acid was soluble in water.

Example 22

An allergen inhibitor containing, as the allergen-inhibiting compound, a sulfonic acid sodium salt of a compound formed by sulfonation of a copolymer of styrene and maleic acid (trade name: "VERSA-TL D72", produced by Akzo Nobel KK, styrene content: 50% by weight, maleic acid content: 50% by weight, sulfonation ratio of styrene: 99 mol % or more, weight average molecular weight (Mw): 20,000) was prepared. Here, the sulfonic acid sodium salt of a compound formed by sulfonation of a copolymer of styrene sulfonic acid and maleic acid was soluble in water.

Example 23

A mixed solution was prepared from 0.4 parts by weight of an aqueous solution containing, as the allergen-inhibiting compound, a homopolymer of sodium p-styrene sulfonate (trade name: "PS-100", produced by Tosoh Organic Chemical Co., Ltd., amount of homopolymer of sodium p-styrene sulfonate: 20% by weight, weight average molecular weight (Mw): 529,000, Z average molecular weight (Mz): 758,000), 0.6 parts by weight of a special silicone binder (trade name: "TF-3500", produced by Hokko Chemical Co., Ltd.), and ion-exchanged water (49 parts by weight).

A cloth composed of polyester fibers (80% by weight) and cotton fibers (20% by weight) was completely immersed in the mixed solution for 2 minutes and then taken out therefrom. Then, the cloth was dried for 10 minutes at 100° C. to give a cloth in which an allergen inhibitor containing the homopolymer of sodium p-styrene sulfonate as the allergen-inhibiting compound was physically fixed on the fibers.

Example 24

A mixed solution was prepared from 0.4 parts by weight of an aqueous solution containing, as the allergen-inhibiting compound, a homopolymer of sodium p-styrene sulfonate (trade name: "PS-50", produced by Tosoh Organic Chemical Co., Ltd., amount of homopolymer of sodium p-styrene sulfonate: 20% by weight, weight average molecular weight (Mw): 390,000, Z average molecular weight (Mz): 618,000), 0.3 parts by weight of a special silicone binder (trade name: "TF-3500", produced by Hokko Chemical Co., Ltd.), 0.3 parts by weight of a urethane binder (trade name: "E-4800", produced by Dai-ichi Kogyo Seiyaku Co., Ltd.), and 49 parts by weight of ion-exchanged water.

A cloth composed of polyester fibers (80% by weight) and cotton fibers (20% by weight) was completely immersed in the mixed solution for 2 minutes and then taken out therefrom. Then, the cloth was dried for 10 minutes at 100° C. to give a cloth in which an allergen inhibitor containing the homopolymer of sodium p-styrene sulfonate as the allergen-inhibiting compound was physically fixed on the fibers.

Example 25

A mixed solution was prepared from 0.5 parts by weight of an aqueous solution of a 20-wt % sulfonic acid sodium salt of a compound formed by sulfonation of polystyrene (trade name: "VERSA-TL502", produced by Akzo Nobel KK, sulfonation ratio: 99 mol % or more, weight average molecular weight: 685,000, Z average molecular weight: 1,153,000) serving as the allergen-inhibiting compound, 0.15 parts by weight of a urethane binder (trade name: "BAYPRET DLP-R", produced by LANXESS K. K.) and 49.35 parts by weight of ion-exchanged water.

A cloth composed of polyester fibers (80% by weight) and cotton fibers (20% by weight) was completely immersed in the mixed solution for 2 minutes and then taken out therefrom. Then, the cloth was dried for 10 minutes at 100° C. to give a cloth in which an allergen inhibitor containing the sulfonic acid sodium salt of the compound formed by sulfonation of polystyrene as the allergen-inhibiting compound was physically fixed on the fibers.

Comparative Example 1

100 parts by weight of ion-exchanged water was prepared.

Comparative Example 2

3 mL of a suspension of a cross-linked agarose support (trade name: "Q Sepharose Fast Flow", produced by Pharmacia Corp.) was prepared.

Comparative Example 3

A cloth composed of polyester fibers (80% by weight) and cotton fibers (20% by weight) was prepared.

Comparative Example 4

Poly(4-vinylphenol) (trade name: "MARUKA LYNCUR M", produced by Maruzen Petrochemical Co., Ltd.) was dissolved in ethanol so as to give a 1-wt % solution.

A cloth composed of polyester fibers (80% by weight) and cotton fibers (20% by weight) was completely immersed in the solution for 2 minutes and then taken out therefrom. Then, the cloth was dried for 10 minutes at 100° C. to give a cloth in which the allergen inhibitor containing poly(4-vinylphenol) was physically fixed on the fibers.

With respect to the solutions of the allergen inhibitor obtained in Examples 1 to 17, the suspensions of the allergen inhibitor obtained in Examples 18 to 20, the allergen inhibitors obtained in Examples 21 and 22, the clothes obtained in Examples 23 to 25, the ion-exchanged water in Comparative Example 1, the suspension of the cross-linked agarose support in Comparative Example 2, and the clothes obtained in Comparative Examples 3 and 4, the allergen-inhibiting performance was evaluated as follows. Tables 1 to 3 show the results. The results according to the undiluted solutions and suspensions in Examples 1 to 19 were shown at the column of "Undiluted" in Table 1.

With respect to the clothes obtained in Examples 23 to 25 and Comparative Examples 3 and 4, light resistance was determined as follows. Table 4 shows the results.

(Allergen-Inhibiting Performance)

A freeze-dried allergen powder (trade name: "Mite Extract-Df", produced by COSMO BIO Co., Ltd.) was dissolved in a phosphate buffer (pH: 7.6) to give an allergen aqueous solution with a protein content of 10 μg/mL.

The solutions of the allergen inhibitor obtained in Examples 1 to 17 were prepared. The suspensions of the allergen inhibitor obtained in Examples 18 to 20 were prepared. The allergen inhibitors obtained in Examples 21 and 22 were prepared. The suspension of cross-linked agarose support obtained in Comparative Example 2 was prepared. The solutions of the allergen inhibitors obtained in Examples 1 to 17 and the suspensions of the allergen inhibitor obtained in Examples 18 and 19 each were diluted 4-fold with ion-exchanged water, and thereby 4-fold diluted solutions of the allergen inhibitors were prepared. The solutions of the allergen inhibitor obtained in Examples 1 to 17 and the suspensions of the allergen inhibitor obtained in Examples 18 and 19 each were diluted 40-fold with ion-exchanged water, and thereby 40-fold diluted solutions of the allergen inhibitor were prepared.

The clothes obtained in Examples 23 to 25 and Comparative Examples 3 and 4 each were cut to give a rectangular test cloth having a size of 2 cm (length)×5 cm (width).

Test tubes each containing 1 mL of the allergen aqueous solution were prepared. The allergen inhibitor solutions, the four-fold diluted solutions of the allergen inhibitor, the 40-fold diluted solutions of the allergen inhibitor, the allergen inhibitor suspensions in Examples 18 to 20, the ion-exchanged water in Comparative Example 1, and the suspension of the cross-linked agarose support in Comparative Example 2 of 100 μL each were added to separate test tubes, and the test tubes were shaken for 24 hours at 37° C. The allergen inhibitors in Examples 21 and 22 of 100 mg, 50 mg, and 20 mg each were added to separate test tubes, and the test tubes were shaken for 24 hours at 37° C.

Test tubes each containing 3.5 mL of the allergen aqueous solution were prepared. The test clothes produced from the clothes in Examples 23 to 25 and Comparative Examples 3 and 4 were put into separate test tubes, and each test cloth was immersed in the allergen aqueous solution. Then, the test tubes were shaken for 24 hours at 37° C.

The allergen aqueous solutions in the test tubes of 100 μL each were supplied to an allergen-determining device (trade name: "Mitey Checker", produced by Sumika Enviro-Science Co., Ltd.), and the degree of coloring on the allergen-determining device was visually observed in each case. The allergen-inhibiting performance was evaluated according to the following criteria. A thicker coloring on the allergen-determining device indicates a higher concentration of the allergens in the solution.

5: A thick, bold, and clear line was observed.

4: A line was clearly observed.

3: Coloring in a linear state was slightly observed.

2: Coloring was slightly observed.

1: No coloring was observed.

(Light Resistance)

The clothes obtained in Examples 23 to 25 and Comparative Examples 3 and 4 were subjected to a test for color fastness to ultraviolet carbon in accordance with JIS L0842 (black panel temperature: 63° C., relative humidity: 50%, irradiation time: 40 hours).

Light resistances of the clothes obtained in Examples 23 to 25 and Comparative Examples 3 and 4 were evaluated by means of a grey scale for assessing change in color. Light resistance was evaluated on 9 scales of 1, 1.5, 2, 2.5, 3, 3.5, 4, 4.5, and 5. The scale 5 indicates that a cloth has the best light resistance, and the scale 1 indicates that a cloth has the worst light resistance.

TABLE 1

| | Solution of allergen inhibitor | | | Allergen-inhibiting compound | |
|---|---|---|---|---|---|
| | Undiluted | 4-Fold diluted | 40-Fold diluted | Mw | Mz |
| Example 1 | 2 | 4 | 5 | 25,000 | 49,000 |
| Example 2 | 2 | 3 | 4 | 109,000 | 200,000 |
| Example 3 | 1 | 1 | 2 | 390,000 | 618,000 |
| Example 4 | 1 | 1 | 2 | 529,000 | 758,000 |
| Example 5 | 1 | 1 | 2 | 386,000 | 588,000 |
| Example 6 | 4 | 5 | 5 | 3,900 | |
| Example 7 | 1 | 1 | 2 | 22,000 | |
| Example 8 | 1 | 1 | 3 | 298,000 | 477,000 |
| Example 9 | 1 | 1 | 2 | 314,000 | 515,000 |
| Example 10 | 1 | 1 | 2 | 487,000 | 828,000 |
| Example 11 | 2 | 3 | 4 | 106,000 | 177,000 |
| Example 12 | 1 | 1 | 2 | 685,000 | 1,153,000 |
| Example 13 | 1 | 2 | 4 | 174,000 | 405,000 |
| Example 14 | 1 | 1 | 2 | 6,000 | |
| Example 15 | 1 | 1 | 2 | 6,000 | |
| Example 16 | 1 | 1 | 3 | 293,000 | 467,000 |
| Example 17 | 1 | 1 | 4 | 329,000 | 521,000 |
| Example 18 | 1 | 2 | 3 | 255,000 | 407,000 |
| Example 19 | 1 | 1 | 2 | 126,000 | |
| Comparative Example 1 | 5 | — | — | | |

TABLE 2

| | Allergen inhibitor | | | Allergen-inhibiting compound | |
|---|---|---|---|---|---|
| | 100 mg | 50 mg | 20 mg | Mw | Mz |
| Example 21 | 2 | 4 | 5 | 20,000 | |
| Example 22 | 1 | 3 | 5 | 20,000 | |

TABLE 3

| | Allergen-inhibiting performance |
|---|---|
| Example 20 | 1 |
| Comparative Example 2 | 5 |

TABLE 4

| | Allergen-inhibiting performance | Light resistance |
|---|---|---|
| Example 26 | 1 | 4.5 |
| Example 24 | 1 | 4.5 |
| Example 25 | 1 | 4.5 |
| Comparative Example 3 | 5 | 4.5 |
| Comparative Example 4 | 1 | 2 |

INDUSTRIAL APPLICABILITY

The allergen inhibitor, the method for inhibiting allergens, and the use as the allergen inhibitor of the present invention hardly cause unpredictable discoloration and discoloration under usual conditions. Thus, they are suitable for applications in which color fading or discoloration due to light occurs, such as interior materials for buildings, articles used inside vehicles, interior materials for vehicles, filters, and textile products.

The invention claimed is:

1. An allergen inhibitor, comprising
an allergen-inhibiting compound including a linear polymer having at least one of substituents at a side chain, the substituents being represented by the formulas (1) to (3):

[Chem. 1]

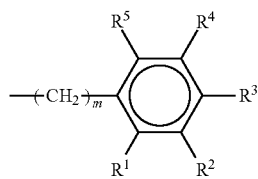

Formula(1)

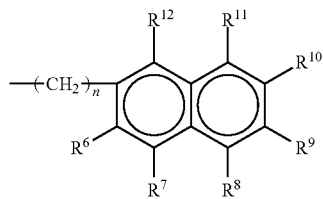

Formula(2)

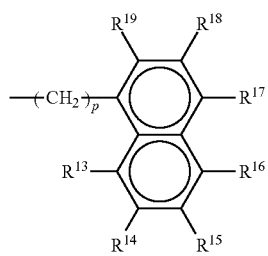

Formula(3)

wherein m, n, and p each represent an integer of 0 to 2; and $R^1$ to $R^{19}$ each represent hydrogen, a carboxyl group, a sulfonic group, an amino group or a derivative of one of them, at least one of $R^1$ to $R^5$ is a carboxyl group, a sulfonic group, an amino group or a derivative of one of them, at least one of $R^6$ to $R^{12}$ is a carboxyl group, a sulfonic group, an amino group, or a derivative of one of them, and at least one of $R^{13}$ to $R^{19}$ is a carboxyl group, a sulfonic group, an amino group or a derivative of one of them, wherein the allergen-inhibiting compound is formed by polymerization or copolymerization of monomers having at least one of the substituents represented by the formulas (1) to (3).

2. An allergen inhibitor, comprising
an allergen-inhibiting compound including a linear polymer having at least one of substituents at a side chain, the substituents being represented by the formulas (1) to (3):

[Chem. 1]

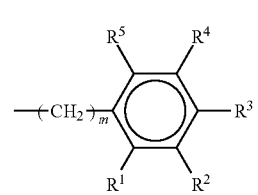

Formula(1)

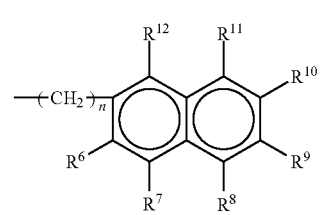

Formula(2)

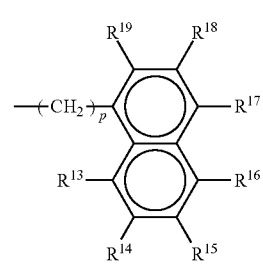

Formula(3)

wherein m, n, and p each represent an integer of 0 to 2; and $R^1$ to $R^{19}$ each represent hydrogen, a carboxyl group, a sulfonic group, an amino group or a derivative of one of them, at least one of $R^1$ to $R^5$ is a carboxyl group, a sulfonic group, an amino group or a derivative of one of them, at least one of $R^6$ to $R^{12}$ is a carboxyl group, a sulfonic group, an amino group, or a derivative of one of them, and at least one of $R^{13}$ to $R^{19}$ is a carboxyl group, a sulfonic group, an amino group or a derivative of one of them, wherein the allergen-inhibiting compound is a compound formed by sulfonation of polystyrene.

3. An allergen inhibitor, comprising
an allergen-inhibiting compound including a linear polymer having at least one of substituents at a side chain, the substituents being represented by the formulas (1) to (3):

[Chem. 1]

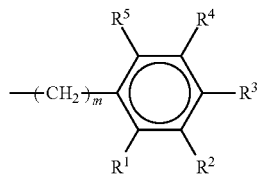

Formula(1)

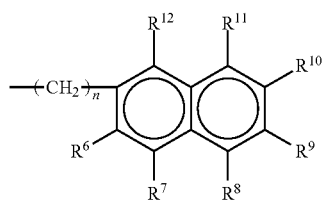

Formula(2)

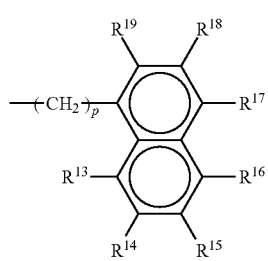

Formula(3)

wherein m, n, and p each represent an integer of 0 to 2; and $R^1$ to $R^{19}$ each represent hydrogen, a carboxyl group, a sulfonic group, an amino group or a derivative of one of them, at least one of $R^1$ to $R^5$ is a carboxyl group, a sulfonic group, an amino group or a derivative of one of them, at least one of $R^6$ to $R^{12}$ is a carboxyl group, a sulfonic group, an amino group, or a derivative of one of them, and at least one of $R^{13}$ to $R^{19}$ is a carboxyl group, a sulfonic group, an amino group or a derivative of one of them, wherein the allergen-inhibiting compound is a sodium salt of a compound formed by sulfonation of polystyrene.

4. The allergen-inhibitor according to claim 1, 2 or 3, wherein the allergen-inhibiting compound is insoluble in water.

5. The allergen-inhibitor according to claim 4, wherein the allergen-inhibiting compound is insoluble in water and is crosslinked by cross-linking of the allergen-inhibiting compound.

6. The allergen-inhibitor according to claim 4, wherein the allergen-inhibiting compound is insoluble in water and fixed to a carrier by fixing of the allergen-inhibiting compound on a carrier.

7. An allergen-inhibiting product comprising an allergen target article treated with the allergen inhibitor of claim 1.

8. The allergen-inhibiting product according to claim 7, wherein the allergen target article is filter, interior material for building, textile product, article used inside vehicle or interior material for vehicle.

9. A method for inhibiting an allergen, comprising applying an allergen inhibitor to a target article with an allergens to inhibit the allergen, the allergen inhibitor comprising an allergen-inhibiting compound including a linear polymer having at least one of substituents at a side chain, the substituents being represented by the formulas (1) to (3):

[Chem. 2]

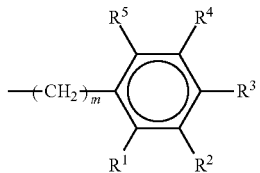

Formula(1)

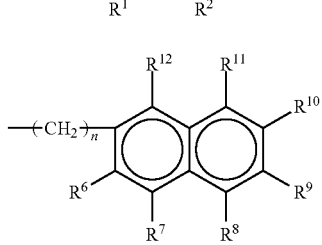

Formula(2)

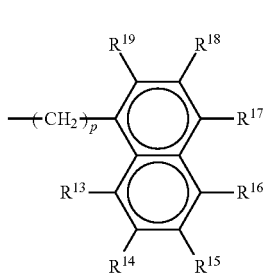

Formula(3)

wherein m, n, and p each represent an integer of 0 to 2; and $R^1$ to $R^{19}$ each represent hydrogen, a carboxyl group, a sulfonic group, an amino group or a derivative of one of them, at least one of $R^1$ to $R^5$ is a carboxyl group, a sulfonic group, an amino group or a derivative of one of them, at least one of $R^6$ to $R^{12}$ is a carboxyl group, a sulfonic group, an amino group or a derivative of one of them, and at least one of $R^{13}$ to $R^{19}$ is a carboxyl group, a sulfonic group, an amino group or a derivative of one of them.

10. A method for inhibiting an allergen, comprising
preliminarily applying an allergen inhibitor to a target article to inhibit allergens sticking to the target article by the action of the allergen-inhibiting compound after the application of the allergen-inhibiting compound to the target article, the allergen inhibitor comprising an allergen-inhibiting compound including a linear polymer having at least one of substituents at a side chain, the substituents being represented by the formulas (1) to (3):

[Chem. 3]

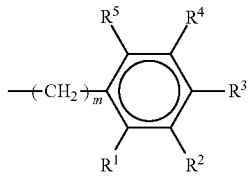

Formula(1)

-continued

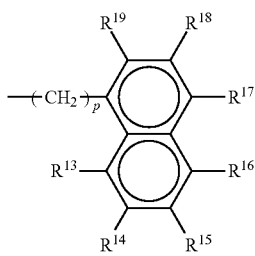
Formula(2)

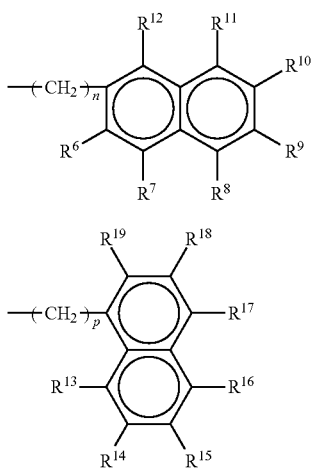
Formula(3)

wherein m, n, and p each represent an integer of 0 to 2; and $R^1$ to $R^{19}$ each represent hydrogen, a carboxyl group, a sulfonic group, an amino group or a derivative of one of them, at least one of $R^1$ to $R^5$ is a carboxyl group, a sulfonic group, an amino group or a derivative of one of them, at least one of $R^6$ to $R^{12}$ is a carboxyl group, a sulfonic group, an amino group or a derivative of one of them, and at least one of $R^{13}$ to $R^{19}$ is a carboxyl group, a sulfonic group, an amino group or a derivative of one of them.

11. The method for inhibiting an allergen according to claim 9 or 10,
wherein the allergen-inhibiting compound is formed by polymerization or copolymerization of monomers having at least one of the substituents represented by the formulas (1) to (3).

12. The method for inhibiting an allergen according to claim 9 or 10,
wherein the allergen-inhibiting compound is a compound formed by sulfonation of polystyrene.

13. The method for inhibiting an allergen according to claim 9 or 10,
wherein the allergen-inhibiting compound is a sodium salt of a compound formed by sulfonation of polystyrene.

14. The method for inhibiting an allergen according to claim 9 or 10,
wherein the allergen-inhibiting compound is insoluble in water.

15. An allergen inhibitor, comprising
an allergen-inhibiting compound including a linear polymer having at least one of substituents at a side chain, the substituents being represented by the formulas (1) to (3):

[Chem. 1]

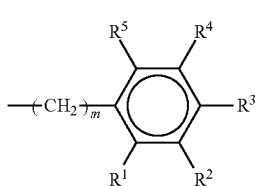
Formula(1)

-continued

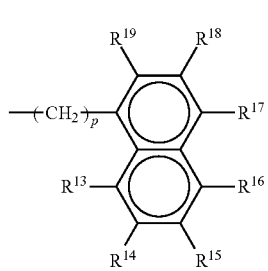
Formula(2)

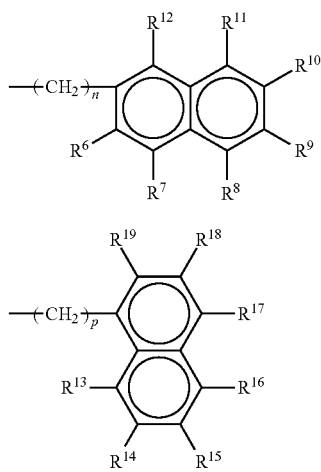
Formula(3)

wherein m, n, and p each represent an integer of 0 to 2; and $R^1$ to $R^{19}$ each represent hydrogen, a carboxyl group, a sulfonic group, an amino group or a derivative of one of them, at least one of $R^1$ to $R^5$ is a carboxyl group, a sulfonic group, an amino group or a derivative of one of them, at least one of $R^6$ to $R^{12}$ is a carboxyl group, a sulfonic group, an amino group, or a derivative of one of them, and at least one of $R^{13}$ to $R^{19}$ is a carboxyl group, a sulfonic group, an amino group or a derivative of one of them,
wherein the allergen-inhibiting compound is a copolymer of a monomer having the substituents represented by the formulas (1) to (3) and a monomer copolymerizable therewith.

16. An allergen inhibitor according to claim 1,
wherein the monomer having the substituents represented by the formulas (1) to (3) is a styrene sulfonic acid or a styrene sulfonic acid salt.

17. The method for inhibiting an allergen according to claim 9 or 10,
wherein the allergen-inhibiting compound is a copolymer of a monomer having the substituents represented by the formulas (1) to (3) and a monomer copolymerizable therewith.

18. The method for inhibiting an allergen according to claim 17,
wherein the monomer having the substituents represented by the formulas (1) to (3) is a styrene sulfonic acid or a styrene sulfonic acid salt.

19. An allergen inhibitor, comprising
an allergen-inhibiting compound including a linear polymer having at least one of substituents at a side chain, the substituents being represented by the formulas (1) to (3):

[Chem. 3]

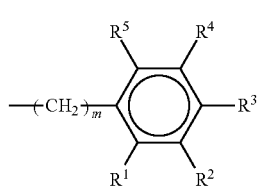
Formula(1)

-continued

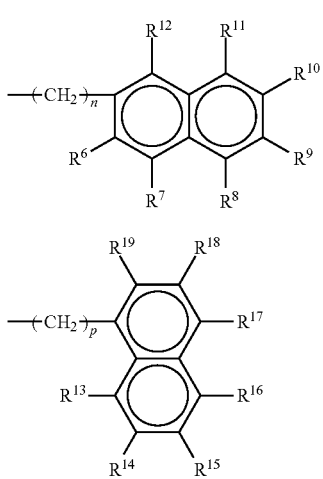

Formula(2)

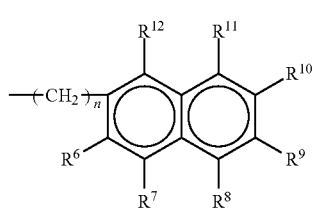

Formula(3)

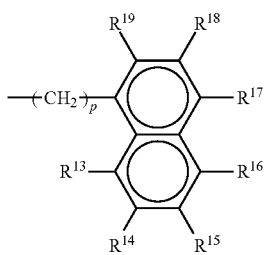

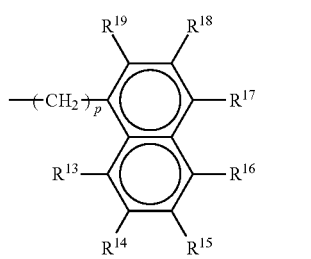

wherein m, n, and p each represent an integer of 0 to 2; and $R^1$ to $R^{19}$ each represent hydrogen, a carboxyl group, a sulfonic group, an amino group or a derivative of one of them, at least one of $R^1$ to $R^5$ is a carboxyl group, a sulfonic group, an amino group or a derivative of one of them, at least one of $R^6$ to $R^{12}$ is a carboxyl group, a sulfonic group, an amino group, or a derivative of one of them, and at least one of $R^{13}$ to $R^{19}$ is a carboxyl group, a sulfonic group, an amino group or a derivative of one of them, wherein the allergen-inhibiting compound is a sulfonated polystyrene.

20. An allergen inhibitor, comprising an allergen-inhibiting compound including a linear polymer having at least one of substituents at a side chain, the substituents being represented by the formulas (1) to (3):

[Chem. 4]

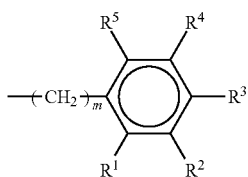

Formula(1)

wherein m, n, and p each represent an integer of 0 to 2; and $R^1$ to $R^{19}$ each represent hydrogen, a carboxyl group, a sulfonic group, an amino group or a derivative of one of them, at least one of $R^1$ to $R^5$ is a carboxyl group, a sulfonic group, an amino group or a derivative of one of them, at least one of $R^6$ to $R^{12}$ is a carboxyl group, a sulfonic group, an amino group, or a derivative of one of them, and at least one of $R^{13}$ to $R^{19}$ is a carboxyl group, a sulfonic group, an amino group or a derivative of one of them, wherein the allergen-inhibiting compound is a sodium salt of a sulfonated polystylrene.

21. The method for inhibiting an allergen according to claim 9 or 10,
wherein the allergen-inhibiting compound is a sulfonated polystylrene.

22. The method for inhibiting an allergen according to claim 9 or 10,
wherein the allergen-inhibiting compound is a sodium salt of a sulfonated polystylrene.

\* \* \* \* \*